(12) United States Patent
Singh

(10) Patent No.: US 7,642,377 B1
(45) Date of Patent: Jan. 5, 2010

(54) SYSTEMS AND METHODS FOR INTEGRATED AMMONIA-UREA PROCESS

(75) Inventor: Vishnu D. Singh, Sugar Land, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 0 days.

(21) Appl. No.: 12/176,534

(22) Filed: Jul. 21, 2008

(51) Int. Cl.
*C07C 273/02* (2006.01)
*C07C 273/04* (2006.01)
*F28D 9/00* (2006.01)
*B01J 8/04* (2006.01)
*B01J 8/00* (2006.01)
*B01J 10/00* (2006.01)
*B01J 10/02* (2006.01)

(52) U.S. Cl. .............................. 564/66; 564/67; 564/70; 564/71; 564/72; 422/187; 422/188; 422/189; 422/196; 422/197; 422/200; 422/201

(58) Field of Classification Search .................. 422/187, 422/188, 189, 196, 197, 200, 201; 564/66, 564/67, 70, 71, 72
See application file for complete search history.

(56) References Cited

U.S. PATENT DOCUMENTS

| 3,303,215 | A | 2/1967 | Otsuka et al. |
|---|---|---|---|
| 3,310,376 | A | 3/1967 | Cook et al. |
| 4,291,006 | A | 9/1981 | Pagani et al. |
| 4,690,812 | A | 9/1987 | Ranke et al. |
| 4,864,059 | A | 9/1989 | Fujii |
| 4,869,887 | A | 9/1989 | Van Dijk |
| 4,988,491 | A | 1/1991 | Van Dijk et al. |
| 5,304,353 | A | 4/1994 | Dente et al. |
| 5,523,483 | A | 6/1996 | Singh et al. |
| 5,684,194 | A | 11/1997 | Pagani |
| 6,231,827 | B1 | 5/2001 | Pagani et al. |
| 6,340,451 | B1 | 1/2002 | Pagani et al. |
| 6,448,441 | B1 | 9/2002 | Wing-Chiu et al. |
| 6,696,026 | B2 | 2/2004 | Pagani et al. |
| 6,723,876 | B2 | 4/2004 | Speth |
| 7,220,882 | B2 | 5/2007 | Porro et al. |

*Primary Examiner*—Peter G O'Sullivan
(74) *Attorney, Agent, or Firm*—KBR IP Legal

(57) ABSTRACT

Systems and methods for producing urea are provided. A method for producing urea can include exchanging heat from a syngas comprising hydrogen and carbon dioxide to a urea solution comprising urea and ammonium carbamate. The heat transferred can be sufficient to decompose at least a portion of the ammonium carbamate. In one or more embodiments, the syngas can be reacted with liquid ammonia to provide a carbon dioxide lean syngas and an ammonium carbamate solution. The ammonium carbamate solution can be heated to a temperature of about 180° C. or more. At least a portion of the ammonium carbamate in the heated ammonium carbamate solution can be dehydrated to provide the urea solution.

20 Claims, 3 Drawing Sheets

SYSTEMS AND METHODS FOR INTEGRATED AMMONIA-UREA PROCESS

BACKGROUND

1. Field

The present embodiments generally relate to systems and methods for producing ammonia and urea. More particularly, embodiments of the present invention relate to systems and methods for the integrated production of ammonia and urea.

2. Description of the Related Art

Urea is synthesized by reacting ammonia and carbon dioxide at high pressure to form ammonium carbamate, which is subsequently dehydrated by applying heat to form urea and water. The reaction of ammonia and carbon dioxide to form urea involve the following equilibrium reactions:

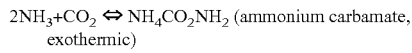

$2NH_3 + CO_2 \Leftrightarrow NH_4CO_2NH_2$ (ammonium carbamate, exothermic)

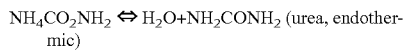

$NH_4CO_2NH_2 \Leftrightarrow H_2O + NH_2CONH_2$ (urea, endothermic)

The first reaction producing ammonium carbamate is an exothermic reaction and essentially goes to completion. The second reaction for producing urea is endothermic and does not go to completion. The conversion of ammonium carbamate to urea increases as the temperature and $NH_3/CO_2$ ratio increase and decreases as the $H_2O/CO_2$ ratio increases. The resulting product can be a urea solution containing urea, water, and unconsumed reactants, which include ammonium carbamate, ammonia, carbon dioxide, and water.

A large part of the ammonia produced throughout the world is utilized for the production of urea. This large use of ammonia has prompted the integration of both the ammonia plant and the urea plant. However, the present ammonia and urea integration schemes, while seemingly attractive, have serious disadvantages. For example, a number pieces of equipment used in the urea production section must be operated at high pressures and temperatures, shutdown of the urea section can necessitate shutdown of the ammonia section, a large amount of energy in the form of heat (e.g. steam) and pressure (e.g. compressors) are required to operate the urea section, and other economically negative impacts are present.

A need, therefore, exists for improved systems and methods for integrated ammonia-urea production.

BRIEF DESCRIPTION OF THE DRAWINGS

So that the manner in which the above recited features of the present invention can be understood in detail, a more particular description of the invention may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION OF THE EMBODIMENTS

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology.

A detailed description will now be provided. Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this patent is combined with available information and technology.

Systems and methods for producing urea are provided. A method for producing urea can include exchanging heat from a syngas comprising hydrogen and carbon dioxide to a urea solution comprising urea and ammonium carbamate. The heat transferred can be sufficient to decompose at least a portion of the ammonium carbamate. In one or more embodiments, the syngas can be reacted with liquid ammonia to provide a carbon dioxide lean syngas and an ammonium carbamate solution. The ammonium carbamate solution can be heated to a temperature of about 180° C. or more. At least a portion of the ammonium carbamate in the heated ammonium carbamate solution can be dehydrated to provide the urea solution.

Figure 1:
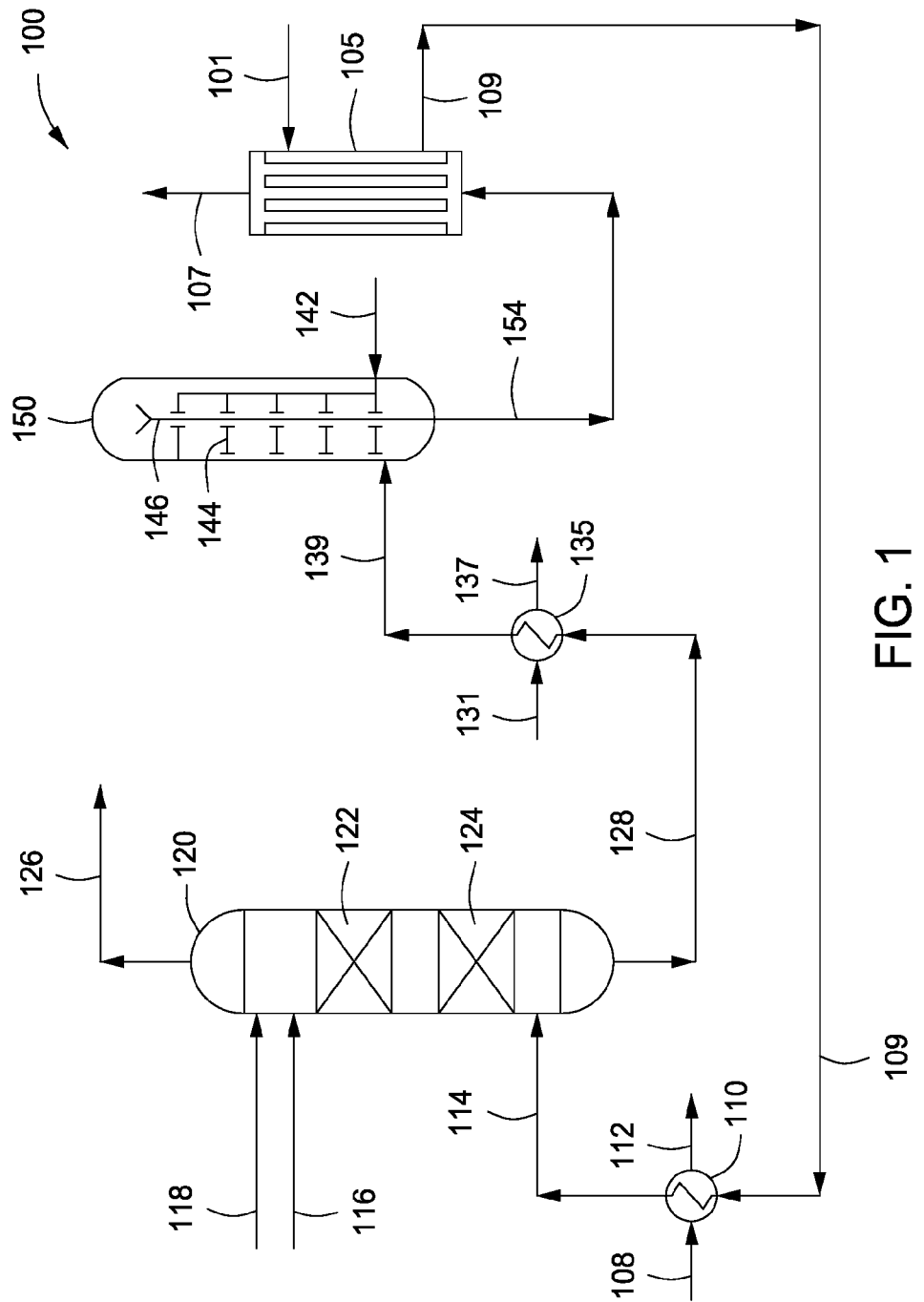
FIG. 1 depicts an illustrative system for purifying syngas and producing urea according to one or more embodiments described.

With reference to the figures, FIG. 1 depicts an illustrative system 100 for purifying syngas and producing urea according to one or more embodiments. In one or more embodiments, the system 100 can include one or more ammonium carbamate decomposers ("decomposer") 105, one or more heat exchangers (two are shown 110, 135), one or more carbon dioxide ("$CO_2$") absorbers 120, and one or more urea reactors 150. In one or more embodiments, the one or more $CO_2$ absorbers 120 can include one or more contact zones (two are shown 122, 124).

In one or more embodiments, heat can be indirectly transferred within the one or more decomposers 105 from a syngas introduced via line 101 to a urea solution introduced via line 154 to provide a heated urea solution via line 107 and a first cooled syngas via line 109. In one or more embodiments, at least a portion of ammonium carbamate in the urea solution can be decomposed to provide ammonia ("$NH_3$") and $CO_2$. In one or more embodiments, the first cooled syngas in line 109 can be further cooled to provide a second cooled syngas in line 114. The first cooled syngas in line 109 or the second cooled syngas in line 114 can be introduced to the one or more $CO_2$ absorbers 120. In one or more embodiments, liquid ammonia via line 116 and water or ammonia/water solution ("aqua ammonia") via line 118 can be introduced to the one or more $CO_2$ absorbers 120.

In one or more embodiments, the liquid ammonia introduced via line 116 to the one or more $CO_2$ absorbers can react with at least a portion of the $CO_2$ in the syngas introduced via line 114 to provide an ammonium carbamate solution via line 128 and a $CO_2$-lean syngas via line 126. In one or more embodiments, the ammonium carbamate solution via line 128 can be introduced to the one or more heat exchangers 135 to provide a heated ammonium carbamate solution via line 139. The heated ammonium carbamate solution via line 139 can be introduced to the one or more urea reactors 150 to provide the urea solution in line 154.

In one or more embodiments, the syngas in line 101 can include, but is not limited to hydrogen, $CO_2$, and nitrogen. In one or more embodiments, the syngas introduced via line 101 can be or include a low temperature shift syngas, a medium temperature shift syngas, a high temperature shift syngas, or any mixture thereof. In one or more embodiments, the hydrogen content of the syngas in line 101 can range from a low of about 45% mol, about 50% mol, or about 55% mol to a high of about 60% mol, about 65% mol, or about 70% mol. In one or more embodiments, the nitrogen content of the syngas in line 101 can range from a low of about 10% mol, about 15% mol, or about 20% mol to a high of about 25% mol, about 30% mol, or about 35% mol. In one or more embodiments, the carbon dioxide content of the syngas in line 101 can range from a low of about 5% mol, about 10% mol, or about 15% mol to a high of about 20% mol, about 25% mol, or about 30% mol. In one or more embodiments, other components of the syngas in line 101 can include, but are not limited to small amounts of argon, carbon monoxide ("CO"), methane, and water.

In one or more embodiments, the syngas in line 101 can be at a temperature ranging from a low of about 200° C., about 210° C., or about 220° C. to a high of about 240° C., about 280° C., or about 300° C. For example the temperature of the syngas in line 101 can be about 225° C., about 230° C., or about 235° C. In one or more embodiments, the syngas can be at a pressure ranging from a low of about 20 kg/cm$^2$, about 30 kg/cm$^2$, or about 35 kg/cm$^2$ to a high of about 80 kg/cm$^2$, about 90 kg/cm$^2$, or about 100 kg/cm$^2$.

In one or more embodiments, the urea solution in line 154 can contain urea, ammonium carbamate, water, and ammonia. In one or more embodiments, the urea content of the urea solution in line 154 can range from a low of about 20% wt, about 24% wt, or about 27% wt to a high of about 31% wt, about 35% wt, or about 40% wt. In one or more embodiments, the $CO_2$ content of the urea solution in line 154 can range from a low of about 7% wt, about 10% wt, or about 12% wt to a high of about 16% wt, about 18% wt, or about 20% wt. In one or more embodiments, the $NH_3$ content of the urea solution can range from a low of about 32% wt, about 35% wt, or about 37% wt to a high of about 40% wt, about 42% wt, or about 45% wt. In one or more embodiments, the water content of the urea solution can range from a low of about 10% wt, about 13% wt, or about 16% wt to a high of about 20% wt, about 22% wt, or about 25% wt. For example, the urea solution in line 154 can contain about 27% wt to about 31% wt urea, about 12% wt to about 16% $CO_2$, about 36% wt to about 40% wt $NH_3$, and about 16% wt to about 20% wt water.

In one or more embodiments, at least a portion of the $CO_2$ and $NH_3$ in the urea solution in line 154 can be in the form of ammonium carbamate ("$NH_4CO_2NH_2$") rather than $CO_2$ and $NH_3$. In one or more embodiments, the $CO_2$ and $NH_3$ contained in the urea solution that can be in the form of $NH_4CO_2NH_2$ can be about 30% wt $NH_4CO_2NH_2$ or more, about 50% wt $NH_4CO_2NH_2$ or more, about 70% wt $NH_4CO_2NH_2$ or more, about 90% wt $NH_4CO_2NH_2$ or more.

In one or more embodiments, the heat indirectly transferred from the syngas to the urea solution within the one or more decomposers 105 can be sufficient to decompose, i.e. dissociate and evaporate, at least a portion of any ammonium carbamate to provide ammonia and carbon dioxide. In one or more embodiments, the one or more decomposers 105 can include any system, device or combination of systems and/or devices suitable for indirectly transferring heat from the syngas introduced via line 101 to the urea solution introduced via line 154. The one or more decomposers 105 can include, but are not limited to one or more U-tube heat exchangers, shell-and-tube heat exchangers, plate-and-frame heat exchangers, or any combination thereof. For example, the one or more decomposers 105 can be a shell-and-tube decomposer where the syngas via line 101 can be introduced to the shell-side of the decomposer 105 and the urea solution can be introduced via line 154 to the tube-side of the decomposer 105.

In one or more embodiments, the syngas recovered via line 109 from the one or more decomposers 105 can be at a temperature of about 150° C. or less, about 110° C. or less, about 90° C. or less, about 75° C. or less, or about 65° C. or less. In one or more embodiments, the heated urea solution in line 107 can be at a temperature ranging from a low of about 170° C., about 175° C., or about 180° C. to a high of about 190° C., about 195° C., or about 200° C. In one or more embodiments, the heated urea solution can be at a pressure ranging from a low of about 70 kg/cm$^2$, about 75 kg/cm$^2$, or about 80 kg/cm$^2$ to a high of about 90 kg/cm$^2$, about 95 kg/cm$^2$, or about 100 kg/cm$^2$. The heated urea solution can contain both $CO_2$ and $NH_3$ as well as $NH_4CO_2NH_2$. In one or more embodiments, the $CO_2$ and $NH_3$ contained in the urea solution that can be in the form of $NH_4CO_2NH_2$ can be about 50% wt $NH_4CO_2NH_2$ or less, about 40% wt $NH_4CO_2NH_2$ or less, about 30% wt $NH_4CO_2NH_2$ or less, or about 20% wt $NH_4CO_2NH_2$ or less.

In one or more embodiments, the one or more decomposers 105 can include additional heat transfer mediums, such as steam, which can be introduced to at least one of the one or more decomposers 105 to further decompose at least a portion of any ammonium carbamate contained in the urea solution before or after indirectly heating the urea solution with the syngas introduced via line 101. For example, steam, which can be at a pressure of about 20 kg/cm$^2$ can be introduced to one or more decomposers 105 to indirectly transfer heat to the urea solution to decompose at least a portion of any ammonium carbamate contained in the urea solution before or after indirectly heating the urea solution with the syngas in line 101. In one or more embodiments, steam or another suitable heat transfer medium can be used rather than the syngas in line 101. For example, steam can be introduced to the one or more decomposers 105 to heat the urea solution introduced via line 154 and the syngas can be cooled in the one or more heat exchangers 110 or if at a suitable temperature can be introduced directly to the one or more $CO_2$ absorbers 120.

In one or more embodiments, the first cooled syngas in line 109 can be, if desired, further cooled in the one or more heat exchangers 110 to provide a second cooled syngas via line 114 at a temperature suitable for introduction to the one or more $CO_2$ absorbers 120. The syngas introduced via line 114, either with further cooling in the one or more heat exchangers 110 or directly from the one or more decomposers 105 can be at a temperature ranging from a low about 30° C., about 50° C., or about 60° C. to a high of about 70° C., about 80° C., or about 90° C. In one or more embodiments, the syngas introduced via line 114 to the one or more $CO_2$ absorbers 120 can be at a pressure ranging from a low of about 20 kg/cm², about 30 kg/cm², or about 35 kg/cm² to a high of about 80 kg/cm², about 90 kg/cm², or about 100 kg/cm².

The one or more heat exchangers 110 can include any system, device, or combination of systems and/or devices suitable for indirectly transferring heat between the syngas to one or more heat transfer mediums. The one or more heat exchangers 110 can include, but are not limited to, one or more U-tube heat exchangers, shell-and-tube heat exchangers, plate-and-frame heat exchangers, or any combination thereof. The heat transfer medium introduced via line 108 to the one or more heat exchangers 110, which can be or include water, for example boiler feed water ("BFW") can be recovered via line 112.

In one or more embodiments, the syngas introduced via line 114 to the one or more $CO_2$ absorbers 120 can react with the ammonia introduced via line 116 to provide the ammonium carbamate solution in line 128 and the $CO_2$-lean syngas in line 126. The one or more contact zones 122, 124 can increase the contact area within the one or more $CO_2$ absorbers 120 between two or more fluids. For example, the one or more contact zones 122, 124 can increase the contact area between the ammonia introduced via line 116 and the $CO_2$, contained in the syngas, introduced via line 114, thereby promoting the formation of the ammonium carbamate and removal of the $CO_2$ from the syngas.

In one or more embodiments, at least a portion of the ammonia introduced via line 116 can be in the liquid phase. The ammonia can be about 75% liquid or more, about 85% liquid or more, about 95% liquid more, about 99% liquid or more, or about 100% liquid. In one or more embodiments, the water introduced via line 118 can be general process water typically available in refinery and or fertilizer plant operations. In one or more embodiments, the water introduced via line 118 can be demineralized water. Demineralized water can be provided by distillation, deionization, membrane filtration, electrodyalisis, or any other demineralization technology. The amount of dissolved solids in the demineralized water can be less than about 10 mg/L, less than about 7 mg/L, less than about 4 mg/L, less than about 2 mg/L, or less than about 1 mg/L.

In one or more embodiments, the one or more $CO_2$ absorbers 120 can be operated at a pressure ranging from a low of about 20 kg/cm², about 25 kg/cm², or about 30 kg/cm² to a high of about 80 kg/cm², about 85 kg/cm², or about 90 kg/cm². In one or more embodiments, the one or more $CO_2$ absorbers can be operated at a pressure ranging from about 35 kg/cm² to about 60 kg/cm², or from about 50 kg/cm² to about 80 kg/cm², or from about 40 kg/cm² to about 70 kg/cm². In one or more embodiments, the one or more $CO_2$ absorbers 120 can be operated at a temperature ranging from a low of about 80° C., about 90° C., or about 100° C. to a high of about 120° C., about 130° C., or about 140° C. For example, the one or more $CO_2$ absorbers 120 can be operated at a temperature of about 100° C., 105° C., about 110° C., about 115° C., or about 120° C.

In one or more embodiments, the one or more contact zones 122, 124, which can be disposed within the one or more $CO_2$ absorbers 120 can include any suitable packing medium, trays, other surface increasing devices, or combinations thereof. In one or more embodiments, the packing medium, trays, and/or other surface increasing devices can be made from any material that can include, but is not limited to any material that is inert to the process. For example, the inert materials can include, ceramic, glass, zirconium, titanium, duplex stainless steels, stainless steel alloys, non-ferrous metals, non-ferrous metal alloys, metal oxides, such as zirconium oxide, or any combination thereof. The particular inert material or materials can be chosen based upon the particular process composition, process conditions, the desired corrosion resistance, and economic factors, such as cost.

In one or more embodiments, the one or more contact zones 122, 124 can be or include, but are not limited to randomly packed material, structured packed material, one or more trays, one or more baffles, or any combination thereof. The randomly packed material can include, but is not limited to Nutter rings, I-rings, P-rings, R-rings, Raschig rings, saddle rings, A-PAK rings, Pall rings, U-rings, or any other known type of packing ring, or a combination thereof. The structured packed material can include, but is not limited to corrugated sheets, crimped sheets, gauzes, grids, wire mesh, monolith honeycomb structures, or a combination thereof. The one or more trays and/or baffles can include, but are not limited to, floating valve trays, fixed valve trays, sieve trays, bubble cap trays, cartridge trays, dual flow trays, baffle trays, shower deck trays, disc and donut trays, orbit trays, horse shoe trays, snap-in valve trays, chimney trays, slit trays, plates, perforated trays, or any combination thereof. Any two adjacent trays can be the same type of tray or different types of trays. The distance or spacing between any two adjacent trays can be the same or different.

In one or more embodiments, the one or more contact zones 122, 124 can include different material, different types of contact enhancing structures, different sizes of materials, and/or different size zones. For example, one contact zone 124 can include randomly packed material and the second contact zone 122 can include structured packed material. In one or more embodiments, any one of the one or more contact zones 122, 124 can include different materials, different types of contact enhancing structures, and/or different sizes of materials within a particular contact zone. For example contact zone 122 can include one or more trays, baffles, randomly packed material, and/or structured packed material. Any two or more contact zones 122, 124 can be the same or different heights. For example the first contact zone 122 can be about 5 m in height and the second contact zone 124 can be about 3 m in height.

In one or more embodiments, the syngas via line 114 can be dispersed or otherwise introduced to the first contact zone 124. The syngas via line 114 can flow through the first and second contact zones 124, 122 counter-currently to the liquid ammonia and water or aqua ammonia which can be introduced via lines 116, 118 to the opposite side of the one or more contact zones 124, 122 as the syngas. In one or more embodiments, the $CO_2$ and ammonia can react within the one or more contact zones 120, or at any point within the $CO_2$ absorber 120, i.e. not within the contact zones 122, 124, to provide ammonium carbonate. In one or more embodiments, the ammonium carbamate solution via line 128 can be recovered and the syngas lean in $CO_2$ can be recovered via line 126.

In one or more embodiments, the syngas introduced via line 114 to the one or more $CO_2$ absorbers 120 and recovered via line 126 can be reduced or free of $CO_2$. For example, the $CO_2$ content of the syngas in line 126 can include less than about 5% mol $CO_2$ dry basis, less than about 3% mol $CO_2$ dry basis, less than about 2% mol $CO_2$ dry basis, or less than about 1% $CO_2$ dry basis. In one or more embodiments, the syngas in line 126 can include less than about 0.7% mol $CO_2$ dry basis, less than about 0.5% mol $CO_2$ dry basis, or less than about 0.3% mol $CO_2$ dry basis. In one or more embodiments, the hydrogen content of the syngas in line 126 can range from a low of about 60% mol dry basis, about 65% mol dry basis, or about 70% mol dry basis to a high of about 75% mol dry basis, 80% mol dry basis, or about 85% mol dry basis. In one or more embodiments, the nitrogen content of the syngas in line 126 can range from a low of about 15% mol dry basis, about 20% mol dry basis, or about 25% mol, dry basis to a high of about 30% mol dry basis, about 35% mol dry basis, or about 40% mol dry basis. In one or more embodiments, the balance of the syngas in line 126 can include, but is not limited to CO, argon, and methane. The balance of the syngas in line 126, on a dry basis, including CO, $CO_2$, argon, and methane can range from a low of about 0.5% mol, about 1% mol, or about 1.5% mol to a high of about 2% mol, about 2.5% mol, or about 3% mol.

In one or more embodiments, the ammonium carbamate solution via line 128 can be introduced to the one or more heat exchangers 135 to be indirectly heated via a heat transfer medium introduced via line 131. In one or more embodiments, heat transfer medium introduced via line 131 can indirectly heat the ammonium carbamate solution introduced via line 128 to provide a heated ammonium carbamate solution via line 139 and a condensate via line 137. The heat transfer medium can be steam. In one or more embodiments, the steam introduced via line 131 can be at a pressure ranging from a low of about 10 kg/cm$^2$, about 15 kg/cm$^2$, or about 18 kg/cm$^2$ to a high of about 22 kg/cm$^2$, about 25 kg/cm$^2$, or about 30 kg/cm$^2$. For example the steam introduced via line 131 can be at a pressure of about 16 kg/cm$^2$, about 20 kg/cm$^2$, or about 24 kg/cm$^2$. Although not shown, the syngas in line 101 can be used to indirectly heat the ammonium carbamate solution in line 128 in the one or more heat exchangers 135 rather than or in addition to heating the urea solution in the one or more heat exchangers 105.

In one or more embodiments, the heated ammonium carbamate solution in line 139 can be at a temperature ranging from a low of about 170° C., about 175° C., or about 180° C. to a high of about 195° C., about 200° C., or about 205° C. In one or more embodiments, the molar ratio of $NH_3$ to $CO_2$ ($NH_3$:$CO_2$) can range from about 3.2:4.4, about 3.4:4.2, or about 3.6:4.

The one or more heat exchangers 135 can include any system, device, or combination of systems and/or devices suitable for indirectly transferring heat from a heat transfer medium introduced via line 131 to the ammonium carbamate solution introduced via line 128. The one or more heat exchangers 135 can include, but are not limited to, one or more U-tube heat exchangers, shell-and-tube heat exchangers, plate-and-frame heat exchangers, or any combination thereof.

In one or more embodiments, the heated ammonium carbamate solution via line 139 can be introduced to the one or more urea reactors 150 to provide the urea solution via line 154. In one or more embodiments, ammonia via line 142 can be introduced via one or more distribution lines 144 that can be disposed throughout at least a portion of the urea reactor 150. The ammonia introduced via line 142 can be at a temperature ranging from a low of about 100° C., about 110° C., or about 120° C. to a high of about 150° C., 170° C., or about 195° C. For example, the ammonia introduced via line 142 can be at a temperature of from about 125° C. to about 140° C.

In one or more embodiments, the urea reactor 150 can be operated at conditions sufficient to provide the urea solution via line 154. In one or more embodiments, the one or more urea reactors 150 can be operated at a pressure ranging from a low of about 180 kg/cm$^2$, about 190 kg/cm$^2$, or about 195 kg/cm$^2$ to a high of about 205 kg/cm$^2$, about 210 kg/cm$^2$, or about 215 kg/cm$^2$. For example, the one or more urea reactors 150 can be operated at a pressure ranging from about 193 kg/cm$^2$ to about 207 kg/cm$^2$ or from about 197 kg/cm$^2$ to about 203 kg/cm$^2$. In one or more embodiments, the urea reactor 150 can be operated at a temperature ranging from a low of about 180° C., about 185° C., or about 190° C. to a high of about 200° C., about 205° C., or about 210° C.

In one or more embodiments, the one or more urea reactors 150 can be heated via the incoming materials, i.e. ammonium carbamate solution via line 139 and the ammonia via line 142. Although not shown, the urea reactor 150 can be heated using one or more heat sources, for example a furnace or stream jacket disposed about at least a portion of the reactor 150, and/or one or more tube coils, a plurality of U-tubes, straight tubes, or bayonet tubes disposed within the urea reactor 150. In one or more embodiments, the one or more tube coils, U-tubes, straight tubes, and/or bayonet tubes can include, but are not limited to one or more fins, static mixers, rifling, heat conductive packing, turbulence causing projections, or any combination thereof.

In one or more embodiments, the at least partial conversion of ammonium carbamate to urea in the one or more urea reactors 150 can be optimized by ensuring a sufficiently long residence time in the reactor. In one or more embodiments, a plurality of trays, baffles, packing, or combinations thereof can ensure or otherwise control the residence time of the ammonium carbamate and the urea produced therefrom. For example, a plurality of trays can prevent or reduce back mixing of the ammonium carbamate and urea produced therefrom. In one or more embodiments, the residence time of the ammonium carbamate solution within the one or more reactors 150 can be less than 2 hours, less than 1 hour, or less than 30 minutes. In one or more embodiments, the residence time can be about 10 minutes or more, about 20 minutes or more, about 30 minutes or more, about 40 minutes or more, or about 50 minutes or more. In one or more embodiments, the at least partially converted ammonia carbamate can be recovered in line 154 via one or more down corners or conduits 146.

Figure 2:
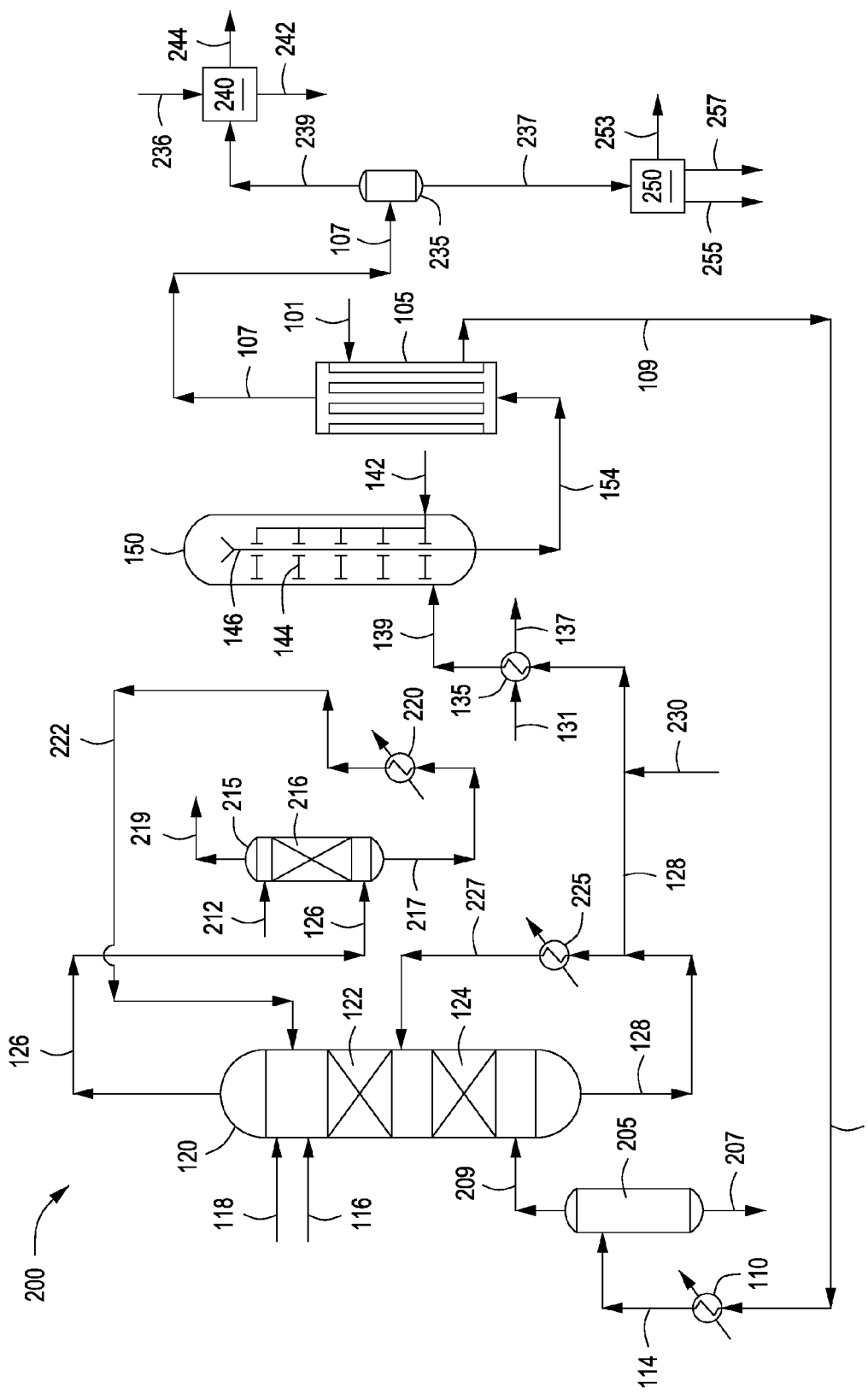
FIG. 2 depicts another illustrative system for purifying syngas and producing urea according to one or more embodiments described.

FIG. 2 depicts another illustrative system 200 for purifying syngas and producing urea according to one or more embodiments. In one or more embodiments, the system 200 can include the one or more decomposers 105, one or more heat exchangers 110, 135, one or more $CO_2$ absorbers 120, and one or more urea reactors 150, which can be as discussed and described above with reference to FIG. 1. In one or more embodiments, the system 200 can further include one or more condensate separators 205, syngas purification units 215, additional heat exchangers (two are shown 220 and 225), high pressure separators 235, ammonium carbamate recovery units 240, and urea purification units 250.

In one or more embodiments, the cooled syngas in line 114 can be introduced to the one or more condensate separators 205 to separate at least a portion of any water present in the cooled syngas via line 207. In one or more embodiments, a syngas via line 209 having a reduced water content can be recovered from the one or more condensate separators 205 and introduced to the one or more $CO_2$ absorbers 120. In one or more embodiments, the one or more condensate separators 205 can be bypassed and the syngas via line 114 can be introduced to the one or more $CO_2$ absorbers 120.

In one or more embodiments, the $CO_2$-lean syngas recovered via line 126 from the one or more $CO_2$ absorbers 120 can be introduced to the one or more syngas purification units 215. In one or more embodiments, the one or more syngas purification units 215 can remove at least a portion of any ammonia that can be contained in the $CO_2$-lean syngas in line 126. The one or more syngas purification units 215 can be any system, device, or combination of systems and/or devices suitable for removing ammonia from the $CO_2$-lean syngas in line 126. For example, the one or more syngas purification units 215 can be or include a water wash column to which water or demineralized water via line 212 can be introduced. The water via line 212 can flow counter-currently to the $CO_2$-lean syngas introduced via line 126 to wash or strip ammonia from the $CO_2$-lean syngas. In one or more embodiments, one or more contact zones 216 can be disposed within the one or more syngas purification units 215. In one or more embodiments, an ammonia/water mixture can be recovered via line 217 and a purified syngas can be recovered via line 219.

In one or more embodiments, the one or more contact zones 216 can be, but are not limited to randomly packed material, structured packed material, one or more trays, one or more baffles, or any combination thereof. The randomly packed material can include, but is not limited to Nutter rings, I-rings, P-rings, R-rings, Raschig rings, saddle rings, A-PAK rings, Pall rings, U-rings, or any other known type of packing ring, or a combination thereof. The structured packed material can include, but is not limited to corrugated sheets, crimped sheets, gauzes, grids, wire mesh, monolith honeycomb structures, or a combination thereof. The one or more trays and/or baffles can include, but are not limited to, floating valve trays, fixed valve trays, sieve trays, bubble cap trays, cartridge trays, dual flow trays, baffle trays, shower deck trays, disc and donut trays, orbit trays, horse shoe trays, snap-in valve trays, chimney trays, slit trays, plates, perforated trays, or any combination thereof. Any two adjacent trays can be the same type of tray or different types of trays. The distance or spacing between any two adjacent trays can be the same or different.

In one or more embodiments, the one or more contact zones 216 can include different material, different types of contact enhancing structures, different sizes of materials, and/or different size zones. For example, one contact zone 216 can include randomly packed material and the second contact zone (not shown) can include structured packed material. In one or more embodiments, any one of the one or more contact zones 216 can include different materials, different types of contact enhancing structures, and/or different sizes of materials within a particular contact zone. For example contact zone 216 can include one or more trays, baffles, randomly packed material, and/or structured packed material.

In one or more embodiments, the ammonia/water mixture via line 217 can be cooled by indirect heat exchange in the one or more heat exchangers 220. Although not shown, the ammonia/water mixture in line 217 can be cooled by direct quenching with water or other suitable cooling medium. In one or more embodiments, at least a portion of the cooled ammonia/water mixture via line 222 can be recycled to the one or more $CO_2$ absorbers 120.

In one or more embodiments, at least a portion of the ammonium carbamate solution in line 128 can be cooled by indirect heat exchange in the one or more heat exchangers 225 to provide a cooled ammonium carbamate solution via line 227. In one or more embodiments, at least a portion of the cooled ammonium carbamate solution via line 227 can be introduced to the one or more $CO_2$ absorbers 120 to increase ammonia absorption.

In one or more embodiments, a recycled ammonium carbamate solution from a downstream processing step, for example the one or more ammonium carbamate recovery units 240 can be introduced via line 230 to the ammonium carbamate solution in line 128. For example, the recycled ammonium carbamate solution via line 230 can be provided from one or more high pressure ammonium carbamate condensers, which can be used in the one or more ammonium carbamate recovery units 240. In one or more embodiments, the heated ammonium carbamate solution in line 139 can be introduced to the one or more urea reactors to provide the urea solution via line 154 as discussed and described above with reference to FIG. 1.

In one or more embodiments, the heated urea solution via line 107 can be introduced to the one or more high pressure separators 235 to provide a first purified urea solution via line 237 and an ammonium carbamate effluent via line 239. The ammonium carbamate effluent can be $NH_3$ and $CO_2$ gas that can separate from the urea solution within the one or more high pressure separators 235.

In one or more embodiments, the urea content of the first purified urea solution in line 237 can range from a low of about 35% wt, about 40% wt, or about 45% wt to a high of about 50% wt, about 55% wt, or about 60% wt. In one or more embodiments, the $NH_3$ content of the first purified urea solution in line 237 can range from a low of about 10% wt, about 15% wt, or about 17% wt to a high of about 23% wt, about 25% wt, or about 30% wt. In one or more embodiments, the $CO_2$ content of the first purified urea solution in line 237 can range from a low of about 2% wt, about 3% wt, or about 4% wt to a high of about 8% wt, about 9% wt, or about 10% wt. In one or more embodiments, the water content of the first purified urea solution in line 237 can range from a low of about 15% wt, about 20% wt, or about 23% wt to a high of about 29% wt, 33% wt, or about 38% wt. The $NH_3$ and $CO_2$ content of the first purified urea solution in line 237 can be $NH_4CO_2NH_2$ as well as both $CO_2$ and $NH_3$.

In one or more embodiments, the separated $NH_3$ and $CO_2$ in line 239 can be introduced to the one or more ammonium carbamate recovery units 240. In one or more embodiments, the one or more ammonium carbamate recovery units 240 can include, but are not limited to one or more high pressure carbamate condensers. In one or more embodiments, BFW can be introduced via line 236 to the one or more ammonium carbamate recovery units 240 to cool the $NH_3$ and $CO_2$ introduced via line 239 to provide ammonium carbamate via line 244 and low pressure steam via line 242. For example, the pressure of the low pressure steam in line 242 can range from a low of about 250 kPa, about 300 kPa, or about 350 kPa to a high of about 500 kPa, about 550 kPa, or about 600 kPa. In one or more embodiments, at least a portion of the ammonium carbamate in line 244 can be introduced via line 230 to the ammonium carbamate solution in line 128. Although not shown, at least a portion of the ammonium carbamate via line 244 can be introduced via line 227 to the one or more $CO_2$ absorbers 120.

In one or more embodiments, the first purified urea solution in line 237 can be introduced to the one or more urea purification units 250 to provide a urea product via line 253, recovered ammonia via line 255, and steam condensate via line 257. The one or more urea purification units 250 can include one or more medium pressure ("MP") ammonium carbamate decomposers, MP ammonium carbamate condensers, $NH_3$ recovery units, low pressure ("LP") ammonium carbamate decomposers, LP ammonium carbamate condensers, one or more vacuum evaporator/separator systems and one or more water removal systems.

In one or more embodiments, the first purified urea solution in line 237 can be introduced to the one or more MP ammonium carbamate decomposers, the one or more MP ammonium carbamate condensers, and the one or more $NH_3$ recovery units to provide a second purified urea solution (not shown) and an ammonium carbamate solution (not shown). In one or more embodiments, the urea content of the second purified urea solution can range from a low of about 50% wt, about 55% wt, or about 59% wt to a high of about 63% wt, about 67% wt, or about 70% wt. The second purified urea solution can contain $NH_4CO_2NH_2$ as well as $CO_2$ and $NH_3$. In one or more embodiments, the $NH_3$ content of the second purified urea solution can range from a low of about 3% wt, about 4% wt, or about 5% wt to a high of about 9% wt, about 10% wt, or about 11% wt. In one or more embodiments, the $CO_2$ content of the second purified urea solution can range from a low of about 1% wt, about 1.3% wt, or about 1.5% wt to a high of about 2% wt, about 2.2% wt, or about 2.5% wt. In one or more embodiments, the water content of the second purified urea solution can range from a low of about 23% wt, about 25% wt, or about 27% wt to a high of about 32% wt, 35% wt, or about 38% wt.

In one or more embodiments, the second purified urea solution can be introduced to the one or more LP ammonium carbamate decomposers and the one or more LP carbamate condensers to provide a third purified urea solution (not shown) and an ammonium carbamate solution (not shown). In one or more embodiments, the urea content of the third urea solution can range from a low of about 60% wt, 65% wt, or about 67% wt to a high of about 73% wt, 75% wt, or about 80% wt. The third purified urea solution can contain $NH_4CO_2NH_2$ as well as $CO_2$ and $NH_3$. In one or more embodiments, the $NH_3$ content of the third purified urea solution can range from a low of about 0.3% wt, about 0.8% wt, or about 1.2% wt to a high of about 1.9% wt, about 2.2% wt, or about 2.5% wt. In one or more embodiments, the $CO_2$ content of the third purified urea solution can range from a low of about 0.5% wt, about 0.1% wt, or about 0.4% wt to a high of about 1% wt, about 1.2% wt, or about 1.3% wt. In one or more embodiments, the water content of the third purified urea solution can range from about 20% wt, about 23% wt, or about 25% wt to a high of about 27% wt, about 30% wt, or about 33% wt.

In one or more embodiments, the third purified urea solution can be introduced to the one or more vacuum evaporator/separator systems and one or more water removal systems to provide a final urea produce via line 253. The urea melt can range from about 95 wt % to 99.9 wt % urea. For example, the urea melt in line 253 can contain about 97% wt to about 99.7% wt urea and from about 0.1% wt to about 3% wt water. The concentration of the urea in the urea melt recovered via line 253 can depend on the number of vacuum separation steps employed and the desired urea melt purity. In one or more embodiments, the urea melt can be further processed to provide urea-formaldehyde resins, melamine, acylureas, urethanes, melamine-formaldehyde, urea prills and granules, derivatives thereof, and combinations thereof. In one or more embodiments, the urea melt in line 253 can be used as a fertilizer or in the synthesis of other fertilizers.

In one or more embodiments, a process condensate via line 257 can be provided from the one or more water removal system, which can contain water, ammonia, carbon dioxide, and urea. In one or more embodiments, the process condensate via line 257 can be sent to a cleanup system (not shown) to provide a purified process condensate, which can be sent off site, or used as boiler feed water for the complex or other uses (not shown). An illustrative cleanup system can include one or more second stage vacuum condensers, water tanks, and desorption and hydrolysis units that can provide a weak carbamate solution and one or more uncondensed gases. The weak carbamate solution can contain water, carbon dioxide, and ammonia. The uncondensed gases can contain carbon dioxide, ammonia, and inerts, such as argon, nitrogen, and/or oxygen. The uncondensed gases can be introduced to an atmospheric scrubber for further scrubbing and/or venting to the atmosphere.

In one or more embodiments, ammonia recovered via line 255 from the ammonia recovery unit (not shown) can be introduced to the one or more urea reactors 150 via line 142, introduced to the one or more $CO_2$ absorbers 120 via line 116, or sent off site for other uses (not shown). In one or more embodiments, the ammonia in line 255 can be indirectly heated in one or more heat exchangers (not shown) to provide heated ammonia suitable for introducing to the one or more urea reactors 150 via line 142, as discussed and described above.

Figure 3:
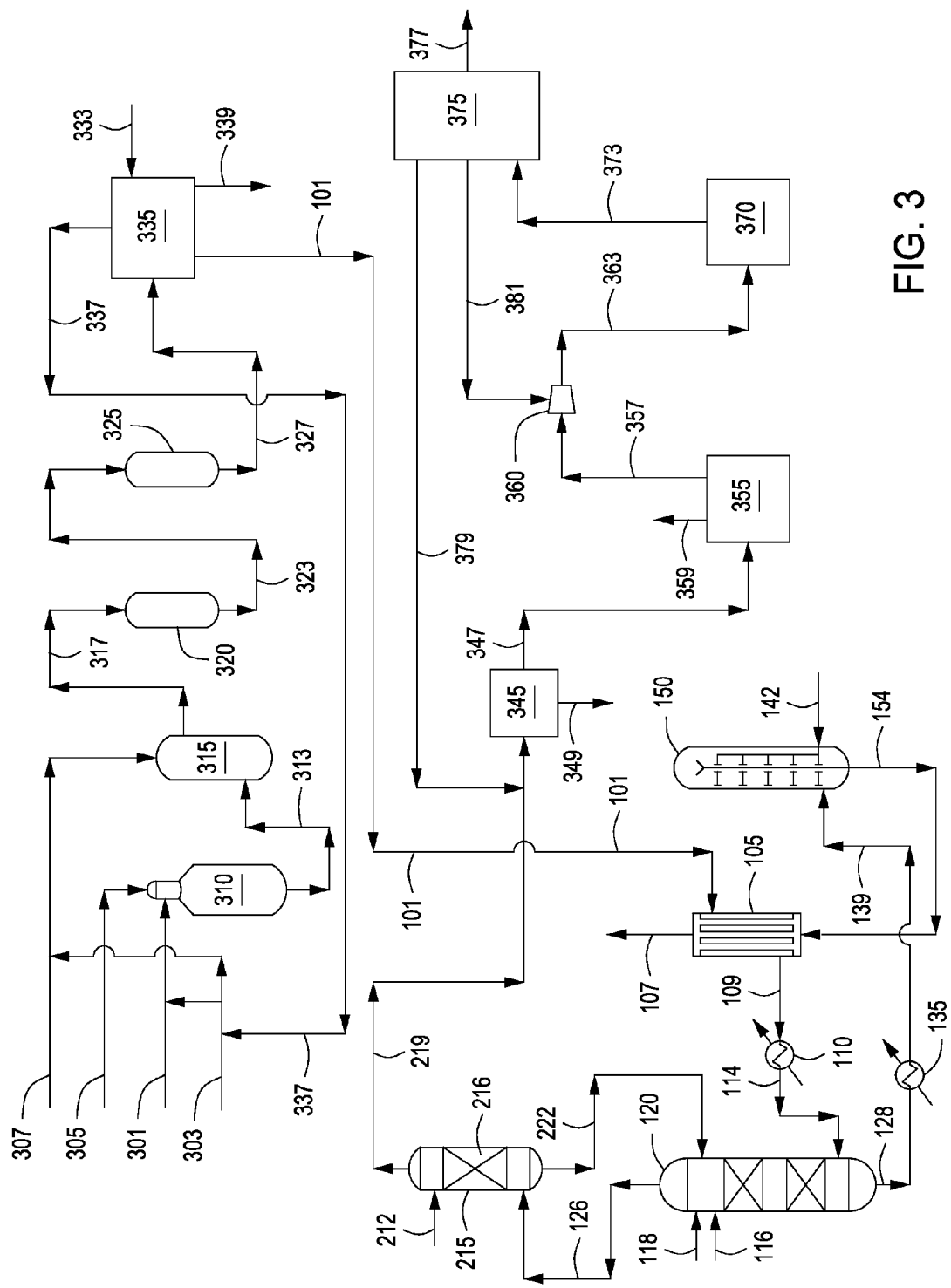
FIG. 3 depicts an illustrative integrated ammonia-urea system according to one or more embodiments described.

FIG. 3 depicts an illustrative integrated ammonia-urea system 300 according to one or more embodiments. In one or more embodiments, the integrated ammonia-urea system ("integrated system") 300 can include the one or more $CO_2$ absorbers 120, the one or more syngas purification units 215, the one or more decomposers 105, and the one or more urea reactors 150, which can be as discussed and described above with reference to FIGS. 1 and 2. In one or more embodiments, the integrated system 300 can further include one or more primary reformers 310, one or more secondary reformers 315, one or more shift converters (two are shown 320, 325), one or more separators 335, one or more methanator/drier units 345, one or more syngas purification units 355, one or more compressors 360, one or more ammonia synthesis units 370, and one or more ammonia condensers 375. In one or more embodiments, the one or more primary reformers 310 and/or the one or more secondary reformers 315 can include one or more catalyst zones having one or more catalysts disposed therein. In one or more embodiments, the one or more shift converters 320, 325 can include one or more catalyst zones having one or more catalysts disposed therein.

In one or more embodiments, a first hydrocarbon via line 301 and an oxidant via line 305 can be introduced to the one or more primary reformers 310 to provide a syngas ("first syngas") via line 313. The one or more primary reformers 310 can be autothermal reformers ("ATR"). At least a portion of the first hydrocarbon can react in the presence of the oxidant and one or more catalysts to provide the first syngas via line 313. In one or more embodiments, steam via line 303 can be introduced to the first hydrocarbon in line 301 as shown, to the oxidant in line 305, directly to the one or more primary reformers 310, or a combination thereof. The first syngas can contain, but is not limited to hydrogen, carbon dioxide, carbon monoxide, nitrogen, argon, water, and methane.

In one or more embodiments, a second hydrocarbon via line 307 can be introduced to the one or more secondary reformers 315 to provide a syngas ("second syngas"). The secondary reformer 315 can be a reforming exchanger. Steam via line 303 can be introduced to the second hydrocarbon in line 307 and/or directly to the one or more secondary reformers 315 (not shown). The second hydrocarbon can react in the presence of the steam and one or more catalysts to provide the second syngas. The second syngas can contain, but is not limited to hydrogen, carbon dioxide, carbon monoxide, water, and methane. As shown, the first syngas in line 313 can be introduced to the secondary reformer 315 to provide at least a portion of the heat necessary for the reforming reactions within the one or more secondary reformers 315. The second hydrocarbon introduced via line 307 can flow through one or more catalyst-containing tubes and the first syngas introduced via line 313 can be introduced to the shell side of the secondary reformer 315. The first syngas introduced via line 313 to the one or more secondary reformers 315 can be mixed with the second syngas within the one or more secondary reformers, as shown, or outside the one or more secondary reformers 315 to provide a raw syngas via line 317.

Although not shown, the first hydrocarbon in line 301, the second hydrocarbon in line 307, or both can be desulfurized prior to introducing the first hydrocarbon and the second hydrocarbon to the primary reformer 310 and/or the secondary reformer 315. Although not shown, the first hydrocarbon in line 301, the second hydrocarbon in line 307, or both can be preheated in one or more preheaters.

Although not shown, the primary reformer 310 can be a steam methane reformer ("SMR") and the secondary reformer can be an ATR. A hydrocarbon via line 301 can be introduced to the SMR, which can provide a first syngas via line 313. The first syngas via line 313 can be compressed and introduced to the SMR and heated to about 370° C. prior to desulfurization. The heated hydrocarbon can be desulfurized to remove at least a portion of any sulfur compounds by hydrogenating the sulfur compounds to hydrogen sulfide via contact with a catalyst that can include cobalt/molybdenum. The desulfurized hydrocarbon can be mixed with steam. The steam can be added in a ratio of about 2.5 to 3.5 moles of steam per mole of carbon in the hydrocarbon to provide a hydrocarbon/water mixture. The hydrocarbon/water mixture can be preheated to about 620° C. in a convection section of the primary reformer.

The heated hydrocarbon/water mixture can be introduced to one or more catalyst-containing tubes disposed within a radiant section of the primary reformer. The catalyst can include, but is not limited to nickel, derivatives thereof, or combinations thereof. The mixture can flow through the catalyst tubes to provide the first syngas in line 313. The first syngas in line 313, when produced via a SMR can contain about 66% $H_2$ mol (dry volume basis) and about 14% mol methane (dry volume basis). The first syngas provided by an SMR can be introduced to an ATR. In addition to the first syngas an oxidant can be introduced to the ATR. Further, additional steam can be introduced to the oxidant to provide a steam to carbon ratio of about 2.5 to 3.5:1. At least a portion of the oxidant can combust to provide heat which can be used to reform the first syngas in the presence of a reforming catalyst to provide the second hydrocarbon. The reforming catalyst can contain, but is not limited to nickel, derivatives thereof, or combinations thereof.

In one or more embodiments, the first hydrocarbon in line 301 and the second hydrocarbon in line 307 (the "hydrocarbons") can include one or more solid, liquid, and/or gaseous hydrocarbons, mixtures thereof, or any combination thereof. In one or more embodiments, the hydrocarbons in line 301 and/or 307 can include one or more commercially available gases, for example methane, propane, or butane. In one or more embodiments, the first hydrocarbon via line 301 and/or the second hydrocarbon via line 307 can contain about 80% mol dry basis methane or more, or about 90% mol dry basis methane or more, or about 95% mol dry basis methane or more, or about 97% mol dry basis methane or more, or about 99% mol dry basis methane or more.

In one or more embodiments, the pressure of the hydrocarbons in lines 301, 307 can range from a low of about 700 kPa, about 1,000 kPa, or about 1,400 kPa to a high of about 4,000 kPa, about 5,000 kPa, or about 5,500 kPa. In one or more embodiments, the pressure of the steam in line 303 can range from a low of about 700 kPa, about 1,000 kPa, or about 1,400 kPa to a high of about 4,000 kPa, about 5,000 kPa, or about 5,500 kPa.

In one or more embodiments, the oxidant in line 305 can be compressed using one or more compressors (not shown) to provide a compressed oxidant in line 305. In one or more embodiments, the oxidant can be air, containing about 21% mol oxygen, about 78% mol nitrogen, and about 1% mol. In one or more embodiments, the oxidant can be oxygen enriched air supplied from an air separation unit (not shown) containing from about 21% mol to about 99% mol oxygen, about 21% mol to about 75% mol or about 21% mol to about 50% mol oxygen, with the balance being nitrogen and lesser quantities of argon. The pressure of the compressed oxidant in line 305 can range from a low of about 700 kPa, about 1,000 kPa, or about 1,400 kPa to a high of about 5,000 kPa, about 7,000 kPa, or about 9,000 kPa. For example, the pressure of the compressed oxidant in line 305 can range from about 2,940 kPa to about 7,850 kPa.

The types and amounts of the oxidant introduced via line 305 to the one or more primary reformers 310 and/or the one or more secondary reformers 315 can influence the composition and physical properties of the first syngas via line 313, the second syngas (not shown), and the syngas via line 317. The one or more oxidants can include, but are not limited to, air, oxygen, essentially oxygen, oxygen-enriched air, mixtures of oxygen and air, water, carbon dioxide, mixtures of oxygen and inert gas such as nitrogen and argon, nitrogen-enriched air, and any mixture thereof. The oxidant can contain about 60% vol oxygen or more, or about 70% vol oxygen or more, or about 80% vol oxygen or more, or about 90% vol oxygen or more, or about 95% vol oxygen or more, or about 99% vol oxygen or more. As used herein, the term "essentially oxygen" refers to an oxidant containing more than 50% vol oxygen. As used herein, the term "oxygen-enriched air" refers to an oxidant stream containing more than 21% vol oxygen. Oxygen, essentially oxygen, or oxygen-enriched air can be obtained, for example, from cryogenic distillation, pressure swing adsorption, membrane separation, or any combination thereof. The one or more oxidants via line 140 can be nitrogen-free or essentially nitrogen-free. As used herein, the term "essentially nitrogen-free," refers to an oxidant stream containing about 5% vol nitrogen or less, 4% vol nitrogen or less, 3% vol nitrogen or less, 2% vol nitrogen or less, or 1% vol nitrogen or less.

In one or more embodiments, the one or more primary reformers 310 and the one or more secondary reformers 315 ("reformers") can include any system, device, or combination of systems and/or devices suitable for reforming a hydrocarbon to provide a gas containing hydrogen, carbon monoxide and/or carbon dioxide. For example, the one or more reformers 310, 315 can be, but are not limited to gasifiers, ATRs, catalytic partial oxidation ("CPOX") reactors, partial oxidation ("POX") reactors, SMRs, and/or reforming exchangers. Depending on the particular reformer and/or arrangement of reformers, the one or more reformers 310, 315 can convert at least a portion of a hydrocarbon in the presence of one or more catalysts, oxidant, heat, flame, steam, or a combination thereof to provide the syngas, e.g. the first syngas and/or the second syngas. In one or more embodiments, the one or more reformers 310, 315 can be arranged in any serial, parallel, or serial/parallel combination.

In one or more embodiments, the one or more reforming exchangers can include a KBR Reforming Exchanger System ("KRES"). Additional KRES process conditions, catalysts, and other details can be found in U.S. Pat. Nos. 5,011,625; 5,122,299; 5,362,454; 6,855,272; 7,138,001; and 7,220,505 all of which are fully incorporated by reference herein. Additional reforming exchanger types, catalyst types, process conditions, and other details can be found in U.S. Pat. Nos. 7,074,347 and 6,224,789.

In one or more embodiments, the hydrogen concentration of the raw syngas in line 317 can range from a low of about 30% mol, about 40% mol, or about 45% mol to a high of about 60% mol, about 70% mol, or about 80% mol. In one or more embodiments, the nitrogen concentration in the raw syngas in line 317 can range from a low of about 10% mol, about 15% mol, or about 20% mol to a high of about 30% mol, about 35% mol, or about 40% mol. In one or more embodiments, the carbon dioxide concentration in the raw syngas in line 317 can range from a low of about 2% mol, about 3% mol, or about 4% mol to a high of about 5% mol, about 6% mol, or about 7% mol. In one or more embodiments, the carbon monoxide concentration in the raw syngas in line 317 can range from a low of about 5% mol, about 10% mol, or about 15% mol to a high of about 25% mol, about 30% mol, or about 35% mol.

In one or more embodiments, the raw syngas in line 317 can be introduced to the shift converter 320 to provide a first converted syngas via line 323. In one or more embodiments, the first converted syngas via line 323 can be introduced to the shift converter 325 to provide a second converted or ("shift converted") syngas via line 327. Water and carbon monoxide can react within the shift converters 320, 325 to form carbon dioxide and additional hydrogen to provide the first converted syngas in line 323 and the shift converted syngas in line 327. Although two shift converters 320, 325 are shown, one shift converter or three or more shift converters can be used.

In one or more embodiments, the one or more shift converters 320, 325 can include any combination of high, medium, and/or low temperature shift converters arranged in any number or configuration including serial, parallel, or serial/parallel combinations. The one or more shift converters 320, 325 can include, but are not limited to single stage adiabatic fixed bed reactors, multiple-stage adiabatic fixed bed reactors with interstage cooling, steam generation or cold quench reactors, tubular fixed bed reactors with steam generation or cooling, fluidized bed reactors, or any combination thereof.

In one or more embodiments, the one or more shift converters 320, 325 can include one or more high temperature shift converters ("HTSC"), one or more medium temperature shift converters ("MTSC"), one or more low temperature shift converters ("LTSC"), or any combination thereof. In one or more embodiments, the raw syngas via line 317 can be introduced to one or more high temperature shift converters 320 to provide the first converted syngas via line 323, which can then be introduced to one or more low temperature shift converters 325 to provide the shift converted syngas via line 327.

In one or more embodiments, the raw syngas via line 323 can be apportioned equally or unequally to any one or more of the HTSCs, MTSCs, LTSCs. For example, about 75% vol of the cooled raw syngas via line 323 can be introduced to a HTSCs and about 25% can be introduced to a MTSC. The converted syngas from the HTSC and the MTSC can then be combined to provide the shift converted syngas in line 327.

In one or more embodiments, the one or more HTSCs, MTSCs, and/or LTSCs can contain one or more catalysts. The one or more HTSCs, MTSCs, and LTSCs can convert carbon monoxide in the cooled raw syngas in line 122 to carbon dioxide by reacting the carbon monoxide in the presence of one or more catalysts within in the one or more HTSCs, MTSCs, and/or LTSCs, at a temperature sufficient to oxidize at least a portion of the carbon monoxide. The catalyst within the one or more HTSCs can include, but is not limited to iron oxide, zinc ferrite, magnetite, chromium oxides, derivatives thereof, or any combination thereof. The one or more HTSCs can be operated at a temperature of from about 325° C. to about 550° C. The catalyst disposed in the one or more MTSCs can include, but is not limited to, iron oxide, chromium oxide, derivatives thereof, or any combination thereof. The one or more MTSCs can be operated at a temperature of from about 250° C. to about 300° C. The catalyst disposed in the one or more LTSCs can include, but is not limited to, copper, zinc, copper promoted chromia, derivatives thereof, or any combination thereof. The one or more LTSC can be operated at a temperature from about 180° C. to about 220° C.

In one or more embodiments, the shift converted syngas in line 327 can be introduced to the one or more separators 335. In one or more embodiments, at least a portion of the water contained in the shift converted syngas in line 327 can be separated or removed via line 337 from the shift converted syngas to provide a syngas via line 101 having reduced water content in respect to the shift converted syngas in line 327. In one or more embodiments, the syngas in line 101 can be the same or similar to the syngas in line 101 discussed and described above in reference to FIGS. 1 and 2.

In one or more embodiments, at least a portion of the separated water via line 337 can be recycled to the steam in line 303 introduced to the first hydrocarbon in line 301 and/or the second hydrocarbon in line 307. In one or more embodiments, the one or more separators 335 can be or include any system, device, or combination of systems and/or devices suitable for separating water from the syngas in line 327. In one or more embodiments, the one or more separators 335 can further include one or more condensate strippers. In one or more embodiments, a process condensate via line 333, for example the process condensate in line 257 (see FIG. 2) can be introduced to one or more condensate strippers, which can remove contaminants to provide a clean process condensate via line 339.

In one or more embodiments, the $CO_2$ contained in the syngas in line 101 can be removed in the one or more $CO_2$ absorbers 120 to provide a syngas via line 126 as discussed and described above with reference to FIGS. 1 and 2. In one or more embodiments, the syngas via line 126 can be introduced to the one or more syngas purification units 215 to provide the purified syngas via line 219 as discussed and described above with reference to FIG. 2.

In one or more embodiments, the purified syngas via line 219 can be introduced to the one or more methanator/drier units 345 to provide a water-lean and/or $CO_2$/CO-lean syngas via line 347. In one or more embodiments, the purified syngas in line 219 can be introduced to the one or more methanators within the one or more methanator/drier units 345 to convert at least a portion of any carbon monoxide and/or carbon dioxide in the purified syngas to methane and water to provide a syngas lean in carbon monoxide and carbon dioxide. For example, the total carbon monoxide and carbon dioxide in the $CO_2$/CO-lean syngas can be less than about 500 ppmw, less than about 200 ppmw, less than about 100 ppmw, less than about 50 ppmw, or less than about 20 ppmw of total carbon monoxide and carbon dioxide. In one or more embodiments, the carbon monoxide and carbon dioxide lean syngas can be recovered via line 347 or can optionally be introduced to the one or more driers within the purification system 345.

In one or more embodiments, the carbon monoxide and carbon dioxide lean syngas can be introduced to the one or more driers within the purification system 135 to provide a dried syngas via line 347 and water via line 349. In one or more embodiments, the carbon dioxide lean syngas in line 219 can be introduced to the one or methanators and the one or more driers in any order or sequence.

In one or more embodiments, the one or more methanator/drier units 345 can provide a syngas via line 347 which can have a hydrogen concentration, dry basis, ranging from a low of about 40% mol, about 50% mol, or about 55% mol to a high of about 75% mol, about 80% mol, or about 85% mol. In one or more embodiments, the syngas in line 347 can have a nitrogen concentration, dry basis, ranging from a low of about 10% mol, about 20% mol, or about 25% mol to a high of about 40% mol, about 50% mol, or about 60% mol. In one or more embodiments, the syngas in line 347 can have a methane concentration, dry basis, ranging from about 0.5% mol to about 10% mol, about 1% mol to about 7% mol, or about 1% mol to about 5% mol. In one or more embodiments, the syngas in line 347 can have an oxygen concentration, dry basis, ranging from about 0.1% mol to about 5% mol, about 0.5% mol to about 4% mol, or about 0.8% mol to about 3% mol. In one or more embodiments, the syngas in line 347 can have an argon concentration, dry basis, ranging from about 0.05% mol to about 2% mol, about 0.1% mol to about 1.5% mol, or about 0.1% mol to about 1% mol. In one or more embodiments, the hydrogen to nitrogen ($H_2:N_2$) molar ratio can range from about 1.5:1 to about 5:1, from about 2:1 to about 4:1, or from about 2.2:1 to about 3.2:1. In one or more embodiments, the $H_2:N_2$ molar ratio can be about 1.6:1, about 1.8:1, about 1.9:1, about 2.1:1, about 2.2:1, about 2.3:1, or about 2.4:1.

In one or more embodiments, the pressure of the syngas in line 347 can range from about 1,000 kPa to about 20,800 kPa, about 2,000 kPa to about 13,700 kPa, or about 3,000 kPa to about 10,400 kPa. In one or more embodiments, the temperature of the syngas in line 347 can range from about −100° C. to about 100° C., about −50° C. to about 50° C., or about −25° C. to about 25° C. In one or more embodiments, the syngas in line 347 can include, but is not limited to, excess nitrogen, hydrogen, oxygen, argon, carbon monoxide, carbon dioxide, mixtures thereof, or any combination thereof.

In one or more embodiments, the one or more methanators within the one or more methanator/drier units 345 can include any one or any combination of physical, mechanical, electrical and/or chemical systems to convert carbon monoxide and carbon dioxide to methane, configured either in series, parallel, or any combination thereof. In one or more embodiments, the one or more methanators can be a catalytic process operating at a temperature sufficient for converting or reacting at least a portion of any carbon monoxide and/or carbon dioxide to methane and water. The one or more catalytic process can include one or more catalytic reactors arranged in series or parallel, containing one or more catalysts suitable for the conversion of carbon monoxide and carbon dioxide to methane. Suitable methanator catalysts can include, but are not limited to, nickel, a rare earth promoted nickel, derivatives thereof, or combinations thereof. The methanator can operate at a temperature of from about 200° C. to about 400° C.

In one or more embodiments, the one or more driers within the one or more methanator/drier units 345 can include, but are not limited to, one or more molecular sieves, absorbents, adsorbents, flash tank separators, incinerators, or any combination thereof. Suitable absorbents can include, but are not limited to, glycol, alkali-earth halide salts, derivatives thereof, or mixtures thereof. Suitable adsorbents can include but are not limited to, activated alumina, silica gel, molecular sieves, activated carbon, derivatives thereof, or mixtures thereof.

In one or more embodiments, the syngas in line 347 can be introduced to the one or more syngas purification systems 355 where one or more contaminants such as argon, oxygen and methane can be removed to provide a contaminant-lean gas mixture or purified syngas via line 357 and a contaminant-rich gas mixture via line 359. The one or more syngas purification systems 355 can be used to remove or separate any contaminants, including excess nitrogen. In one or more embodiments, the one or more purification systems 355 can include one or more cryogenic-type separators operating at a temperature less than about −150° C. The one or more contaminants and/or excess nitrogen can be removed from the one or more syngas purification systems 355 as a waste gas via line 359. Additional process conditions and other details can be found in U.S. Pat. No. 7,090,816 and U.S. Patent Publication No.: 2006/0239871.

In one or more embodiments, the $H_2:N_2$ molar ratio of the purified syngas in line 357 can range from about 2:1 to about 4:1 or from about 2.2:1 to about 3.2:1. For example, the $H_2:N_2$ molar ratio can be about 2.9:1, about 3:1, about 3.1:1, or about 3.2:1. The hydrogen concentration in the purified syngas can range from about 50% mol to about 90% mol, about 60% mol to about 85% mol, or about 70% mol to about 80% mol. The nitrogen concentration in the purified syngas in line 357 can range from about 10% mol to about 40% mol, about 15% mol to about 35% mol, or about 20% mol to about 30% mol. The methane concentration in the purified syngas in line 142 can range from about 0.001% mol to about 0.05% mol, about 0.002% mol to about 0.03% mol, or about 0.005% mol to about 0.01% mol. The oxygen concentration in the purified syngas in line 142 can range from about 0.001% mol to about 0.05% mol, about 0.002% mol to about 0.03% mol, or about 0.005% mol to about 0.01% mol. The argon concentration in the purified syngas in line 142 can range from about 0.05% mol to about 2% mol, about 0.1% mol to about 1.5% mol, or about 0.1% mol to about 1% mol.

In one or more embodiments, the purified syngas via line 357 can be introduced to the one or more compressors 360 to provide a compressed syngas via line 363. In one or more embodiments, the compressed syngas in line 363 can be at a pressure ranging from a low of about 1,000 kPa, about 2,000 kPa, or about 3,000 kPa to a high of about 10,400 kPa, about 13,700 kPa, or about 20,800 kPa. In one or more embodiments, the temperature of the compressed syngas via line 357 can range from about −100° C. to about 100° C., about −50° C. to about 50° C., or about −25° C. to about 25° C.

In one or more embodiments, the compressed syngas via line 363 can be introduced to the one or ammonia synthesis units 370. In the one or more ammonia synthesis units 370 at least a portion of the nitrogen and hydrogen present in the purified syngas introduced via line 363 can combine, to provide an ammonia product via line 373. In one or more embodiments, unreacted hydrogen and/or nitrogen can be present in line 373. In one or more embodiments, the one or more ammonia synthesis units 370 can be conventional single or multi-pass converters using one or more magnetite catalysts. In one or more embodiments, the one or more ammonia synthesis units 370 can be single or multi-pass converters using one or more noble metal catalysts, or one or more catalysts based upon ruthenium, such as the ruthenium-based KAAP catalyst available from Kellogg, Brown and Root. The use of one or more higher activity, noble metal, catalysts can allow the use of lower pressures within the ammonia synthesis loop, thereby permitting use of a single barrel ammonia compressor 360. In one or more embodiments, the ammonia concentration in line 373 can range from a low of about 1% mol, about 3% mol, or about 5% mol to a high of about 20% mol, about 30% mol, or about 40% mol.

In one or more embodiments, the one or more ammonia synthesis units 370 can include any reactor intended to operate at elevated pressures and/or temperatures to convert at least a portion of a feed gas containing nitrogen and hydrogen to ammonia. In one or more embodiments, the one or more ammonia synthesis units 370 can include one or more "Split-Flow Ammonia Converters" as described in U.S. Pat. No. 7,081,230. In one or more embodiments, the one or more ammonia synthesis units 370 can include one or more "Isothermal Ammonia Converters" as described in U.S. Pat. No. 6,171,570. In one or more embodiments, the one or more ammonia synthesis units 370 can include one or more "Horizontal Ammonia Converter Adapted for High Activity Catalyst" as described in U.S. Pat. No. 6,132,687. In one or more embodiments, the one or more ammonia synthesis units 370 can include one or more ammonia converters as described in U.S. patent application Ser. No. 12/107,506, which is incorporated by reference herein.

In one or more embodiments, the ammonia product in line 373 can be introduced to the one or more ammonia condensers 375. In the one or more ammonia condensers 375, the ammonia can be condensed and concentrated to provide an ammonia product via line 377, a first recycle via line 379, and a second recycle via line 381. In one or more embodiments, the first recycle line 379 can be introduced to the purified syngas in line 219 before the one or more methanator/drier units 345, the methanator, the drier, or a combination thereof. In one or more embodiments, the second recycle in line 381 can be introduced to the purified syngas in line 357, the one or more compressors 360, or both. Although not shown, a warm $NH_3$ produce and a cold $NH_3$ product can be recovered from the one or more ammonia condensers 375.

In one or more embodiments, the ammonia concentration of the ammonia product in line 377 can be about 85% wt, about 90% wt, about 95% wt, or about 99.9% wt. In one or more embodiments, the ammonia product in line 377 contain a maximum of about 15% wt, about 10% wt, about 5% wt, or about 0.1% wt of combined hydrogen and nitrogen.

In one or more embodiments, at least a portion of the hydrogen and/or nitrogen can be removed from the one or more ammonia condensers 375 via the first recycle via line 379. The hydrogen concentration in the first recycle in line 379 can range from a low of about 40% mol, about 50% mol, or about 60% mol to a high of about 80% mol, about 85% mol, or about 90% mol. The nitrogen concentration in the first recycle in line 379 can range from a low of about 10% mol, about 15% mol, or about 20% mol to a high of about 40% mol, about 50% mol, or about 60% mol.

In one or more embodiments, at least a portion of the hydrogen and/or nitrogen can be removed from the one or more ammonia condensers 375 via the second recycle via line 381. The hydrogen concentration in the second recycle in line 381 can range from a low of about 40% mol, about 50% mol, or about 60% mol to a high of about 80% mol, about 85% mol, or about 90% mol. The nitrogen concentration in the second recycle in line 381 can range from a low of about 10% mol, about 15% mol, or about 20% mol to a high of about 40% mol, about 50% mol, or about 60% mol.

In one or more embodiments, the one or more ammonia condensers 375 can include any mechanical or chemical system capable of selectively separating ammonia from a gas mixture including at least hydrogen and nitrogen. In one or more embodiments, the one or more ammonia condensers 375 can include one or more cryogenic purifiers containing one or more refrigeration exchangers and one or more refrigeration compressors.

In one or more embodiments, at least a portion of the ammonia product via line 377 can be introduced to the one or more $CO_2$ absorbers 120 via line 116. In one or more embodiments, the warm ammonia product and/or the cold ammonia product via line 377 can be introduced to one or more $CO_2$ absorbers 120.

Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A method for producing urea comprising:
   exchanging heat from a syngas comprising hydrogen and carbon dioxide to a urea solution comprising urea and ammonium carbamate, wherein the heat transferred is sufficient to decompose at least a portion of the ammonium carbamate;
   reacting the syngas with liquid ammonia to provide a carbon dioxide lean syngas and an ammonium carbamate solution;
   heating the ammonium carbamate solution to a temperature of about 180° C. or more; and
   dehydrating at least a portion of the ammonium carbamate in the heated ammonium carbamate solution to provide the urea solution.

2. The method of claim 1, wherein the syngas and liquid ammonia are reacted at a pressure of from about 35 kg/cm² to about 80 kg/cm² and a temperature of from about 100° C. to about 120° C.

3. The method of claim 1, wherein the ammonium carbamate solution is indirectly heated using steam, wherein the steam is at a pressure of about 15 kg/cm² to about 25 kg/cm².

4. The method of claim 1, wherein the ammonium carbamate is dehydrated at a temperature of from about 190° C. to about 200° C. and a pressure of from about 195 kg/cm² to about 205 kg/cm² and wherein the ammonium carbamate is dehydrated in the presence of ammonia.

5. The method of claim 1, wherein the syngas and the liquid ammonia are reacted in the presence of water and at least a portion of a reflux, wherein the reflux comprises at least a portion of the ammonium carbamate solution.

6. The method of claim 1, wherein the carbon dioxide lean syngas is contacted with water to remove at least a portion of any residual ammonia.

7. The method of claim 1, wherein at least a portion of the carbon dioxide lean syngas is reacted in the presence of one or more catalysts to provide an ammonia product.

8. A method for producing urea comprising:

exchanging heat from a syngas comprising at least 12% mol carbon dioxide to a first solution comprising about 27-31% wt urea, about 20-25% wt ammonium carbamate, about 27-31% wt ammonia, about 0-4% wt $CO_2$, and about 16-20% wt water, wherein the heat transfer is sufficient to decompose at least a portion of the ammonium carbamate;

reacting the cooled syngas comprising at least 12% mol carbon dioxide with liquid ammonia in the presence of water to provide a second solution comprising about 65-75% wt ammonium carbamate, about 22-25% wt water, and less than about 5% wt ammonia and a syngas comprising at least 20% mol nitrogen, at least 65% mol hydrogen and less than 3% mol carbon dioxide;

heating the second solution to a temperature of at least 180° C.; and dehydrating at least a portion of the ammonium carbamate in the heated second solution to provide the first solution.

9. The method of claim 8, wherein the cooled syngas and liquid ammonia are reacted in the presence of water and a reflux, wherein the reflux comprises at least a portion of the second solution.

10. The method of claim 9, wherein the reflux is first cooled by heating ammonia recovered from one or more downstream first solution purification steps, boiler feed water or both.

11. The method of claim 8, wherein at least a portion of the ammonium carbamate in the heated solution is dehydrated in the presence of ammonia.

12. The method of claim 11, wherein the ammonia comprises ammonia recovered from a downstream processing step.

13. The method of claim 8, wherein at least a portion of the syngas comprising at least 20% mol nitrogen and at least 65% mol hydrogen is reacted in the presence of one or more catalysts to provide an ammonia product.

14. The method of claim 13, wherein the one or more catalysts comprise iron, ruthenium, rhodium, palladium, osmium, iridium, platinum, derivatives thereof, or combinations thereof.

15. The method of claim 13, wherein the syngas comprising at least 20% mol nitrogen and at least 65% mol hydrogen is contacted with water to remove at least a portion of any residual ammonia.

16. The method of claim 8, wherein at least a portion of the decomposed ammonium carbamate is reacted to provide ammonium carbamate and heat.

17. The method of claim 16, wherein at least a portion of the heat is indirectly exchanged with a condensate to provide steam, wherein the steam is at a pressure of at least 10 kg/cm$^2$.

18. The method of claim 8, wherein the heated second solution is at a pressure of from about 190 kg/cm$^2$ to about 210 kg/cm$^2$.

19. The method of claim 8, wherein the second solution is heated with steam at a pressure of about 20 kg/cm$^2$.

20. A system for producing urea comprising:

one or more ammonium carbamate decomposers adapted to exchange heat from a syngas comprising at least 12% carbon dioxide to a first solution comprising about 27-31% wt urea, about 20-25% wt ammonium carbamate, about 27-31% wt ammonia, about 0-4% wt carbon dioxide, and about 16-20% wt water, wherein the heat transfer is sufficient to decompose at least a portion of the ammonium carbamate;

one or more carbon dioxide absorbers adapted to react the cooled syngas comprising at least 12% carbon dioxide with liquid ammonia in the presence of water to provide a second solution comprising about 65-75% wt ammonium carbamate, about 22-25% wt water, and less than about 5% wt ammonia and a syngas comprising at least 20% mol nitrogen, at least 65% mol hydrogen and less than 3% mol carbon dioxide;

one or more heat exchangers adapted to heat the second solution to a temperature of at least 180° C.; and one or more reactors adapted to dehydrate at least a portion of the ammonium carbamate in the heated solution to provide the first solution.

\* \* \* \* \*